(12) United States Patent
Foster

(10) Patent No.: US 7,569,157 B2
(45) Date of Patent: Aug. 4, 2009

(54) ROTTED WOOD STABILIZER COMPOSITION AND METHODS OF MAKING AND USING SAME

(75) Inventor: Van R. Foster, Westerville, OH (US)

(73) Assignee: Hunt Holdings, Inc., Wilmington, DE (US)

( * ) Notice: Subject to any disclaimer, the term of this patent is extended or adjusted under 35 U.S.C. 154(b) by 573 days.

(21) Appl. No.: 11/158,375

(22) Filed: Jun. 22, 2005

(65) Prior Publication Data

US 2006/0289835 A1 Dec. 28, 2006

(51) Int. Cl.
*C09K 15/06* (2006.01)
*C09D 15/02* (2006.01)
*C09D 15/14* (2006.01)
*C09D 15/16* (2006.01)

(52) U.S. Cl. .............. 252/399; 252/182.13; 252/182.18; 252/182.24; 106/12; 106/15.05

(58) Field of Classification Search .............. 252/182.13
See application file for complete search history.

(56) References Cited

U.S. PATENT DOCUMENTS

| | | | |
|---|---|---|---|
| 3,714,099 A | 1/1973 | Biale | |
| 3,714,100 A | 1/1973 | Biale et al. | |
| 3,856,734 A | 12/1974 | Iacoviello | |
| 3,877,979 A | 4/1975 | Clark | |
| 4,080,479 A | 3/1978 | Vamvacas | |
| RE31,576 E | 5/1984 | Hilditch | |
| 4,496,613 A | 1/1985 | Zagefka et al. | |
| 4,778,833 A | 10/1988 | Van der Drift et al. | |
| 4,929,668 A * | 5/1990 | Zeibig et al. | 524/745 |
| 5,023,247 A * | 6/1991 | Boulanger et al. | 514/89 |
| 5,092,953 A | 3/1992 | Derby et al. | |
| 5,182,328 A | 1/1993 | Iacoveillo et al. | |
| 5,304,237 A | 4/1994 | Barth et al. | |
| 5,416,140 A * | 5/1995 | Columbus et al. | 524/13 |
| 5,869,590 A * | 2/1999 | Clark et al. | 526/323 |
| 6,162,850 A * | 12/2000 | Boucher et al. | 524/405 |
| 6,262,149 B1* | 7/2001 | Clark et al. | 523/501 |
| 6,444,134 B1* | 9/2002 | Holman et al. | 216/29 |
| 2002/0037957 A1 | 3/2002 | Liao et al. | |
| 2003/0017269 A1* | 1/2003 | Schierlmann | 427/325 |
| 2003/0125471 A1* | 7/2003 | Ishihara et al. | 525/326.8 |
| 2003/0162880 A1 | 8/2003 | Rabasco et al. | |
| 2004/0082706 A1 | 4/2004 | Tsai et al. | |
| 2004/0115350 A1* | 6/2004 | Bolton et al. | 427/262 |
| 2005/0037202 A1 | 2/2005 | Hejna et al. | |
| 2005/0203219 A1* | 9/2005 | Guo et al. | 524/17 |
| 2006/0287416 A1* | 12/2006 | Schellenberg et al. | 524/100 |

* cited by examiner

*Primary Examiner*—Joseph D Anthony
(74) *Attorney, Agent, or Firm*—McNees Wallace & Nurick LLC

(57) ABSTRACT

A rotted wood stabilizer composition is provided, the composition comprising: from about 75 to about 90 weight percent of a crosslinking polymer; from about 1.5 to about 0.5 to about 1.5 weight percent of a film forming agent, and from about 8 to about 15 weight percent water, and optionally further comprising a biocide and a defoamer. The composition preferably has a pH in the range of from about 2.8 to about 3.0. Further the composition preferably has a viscosity of between about 750 to about 1250 cps as measured on a BROOKFIELD RV viscometer (helipath on) with a #2 T/E spindle at about 12 rpm and about 25° C. The invention further provides for methods of manufacturing the composition, as well as for methods of repairing a rotted area of a wood component by applying the composition of the present invention.

14 Claims, No Drawings

ROTTED WOOD STABILIZER COMPOSITION AND METHODS OF MAKING AND USING SAME

TECHNICAL FIELD OF THE INVENTION

The present invention is directed towards rotted wood stabilizer compositions. Specifically, the present invention is directed towards waterborne rotted wood stabilizer compositions that are non-toxic and non-flammable, as defined by the Federal Hazardous Substances Act.

BACKGROUND OF THE INVENTION

During the repair of a wooden structure that has suffered from rot, it is not only necessary to remove the wood that has been affected by rot, but it is also important to treat and/or strengthen the area before applying a repair product such as a wood filler. This is necessary so a strong bond can be formed by the wood filler to the area to be repaired and also so any wood softened by rot that could not be easily removed by scraping will be structurally strong before the repair is made.

Presently there are a few rotted wood stabilizers on the market. These compositions can generally be classified into one of two categories. The first category comprises solventborne (i.e. containing organic liquids as the solvent, such as alcohols, acetones, ketones, etc.) rotted wood stabilizer compositions. The second category comprises waterborne rotted wood stabilizer compositions, such as PC Petrifier Rotted Wood Hardener sold by Protective Products Corp. of Allentown, Pa. 18102.

The current leader in the solventborne rotted wood stabilizer market is Bondo Corporation of Atlanta, Ga. Bondo's wood rot stabilizer product is an extremely flammable rotted wood stabilizer that is a polystyrene resin dissolved in acetone and methyl ethyl ketone (MEK). In essence, the Bondo's stabilizer is little more than "airplane glue" thinned down to a very low viscosity liquid having relatively low solids by weight percent. The low-viscosity Bondo product can be poured from a container and will flow into a crevice of rotted wood. Upon drying, it will penetrate the wood and strengthen the rotted wood area. However, multiple treatments are required, primarily because organic solventborne stabilizers have a lower solids content, which delivers low volume of solids upon application. Therefore, multiple applications or coats are often necessary to fully treat a repair area.

Solventborne products allow for fast evaporation and will dry at the same rate, independent of atmospheric humidity. However, this advantage is offset by the disadvantages. In addition to the fact that multiple coatings are required in order to strengthen the rotted wood area, known solventborne rotted wood stabilizers are extremely flammability and create a safety hazard. Fumes from solventborne rotted wood stabilizer compositions present an immediate exposure hazard to the users and others in close proximity to the application, as well as a flame hazard due to the high flammability and low flash point of the solvents used in the composition. Additionally, the use of organic solvents in known compositions presents an environmental hazard in the form of potential product spills, improper application, and leaching from treated wood into the surrounding environment With respect to waterborne wood stabilizers, the MSDS for Protective Coating's PC Petrifier™ brand wood hardener indicates that it is a water-based mixture of a urethane hybrid polymer, acrylic latex, sodium dioctylsulfosuccinate, and 1-methyl-2-pyrrolidinone. The labeling and advertising for PC Petrifier™ indicates that it is not recommended for structural repairs, and therefore it does not address the need for a water-based wood stabilizing composition that can effect a structural repair. Additionally, without a film-forming agent and biocide, repairs using known waterborne products such as the PC Petrifier™ product are compromised by poor penetration and inadequate protection against recurring infestation of mold and other organisms.

SUMMARY OF THE INVENTION

The present invention overcomes many of the disadvantages of prior art solventborne rotted wood stabilizers. Rotted wood stabilizers of the present invention are non-flammable; offer improved durability with excellent adhesion and dried structural integrity; and readily accept wood fillers as additional layers in a repaired wooden component.

Compared to known rotted wood stabilizers, the present invention offers better water resistance, improved overlayer acceptance, and improved durability. The present compositions are based on a waterborne crosslinking polymer emulsion. The compositions are not flammable because water is used as the vehicle to carry the polymer for delivery to a desired surface. The present compositions also have an appreciably higher weight percent of solids than known solventborne products, with the advantage that one application of the composition is required as compared to multiple applications of the solventborne competitors' compositions.

In one embodiment, a rotted wood stabilizer composition of the present invention comprises the following elements: a crosslinking polymer, a film-forming agent, and water. Optionally, the composition further includes a biocide such as a mildewcide, bactericide, and/or fungicide, and optionally also a defoamer.

In another embodiment, methods are provided for manufacturing a waterborne wood stabilizer composition that comprises a crosslinking polymer and a film-forming agent. In the preferred embodiment, the method comprises the steps of: (a) providing a mixing vessel; (b) placing water, a defoamer, and at least one crosslinking polymer emulsion in the mixing vessel under slow agitation; (c) mixing this combination of ingredients until substantially homogeneous; (d) adding at least one film-forming agent to the mixing vessel while agitating; (e) mixing the contents of the mixing vessel until substantially homogeneous; and (f) adding water and to the mixing vessel while agitating in sufficient quantity so as to produce a rotted wood stabilizer composition having a desirable viscosity.

In yet another embodiment, methods are provided for repairing a wood component having at least one rotted area. The preferred method comprises the steps of providing a wood component having a rotted area, providing a wood stabilizer composition in an aqueous carrier, the composition comprised of a crosslinking polymer and a film-forming liquid. The method involves applying the composition to the rotted area, and allowing the composition to dry to form a structurally stabilized repaired area. Additionally, the methods of the preset invention optionally provide that once the waterborne composition is applied and cured to fill and seal the area in question, the repaired area may be further repaired, such as by applying a stainable wood filler, for instance.

In addition to the novel features and advantages mentioned above, other objects and advantages of the present invention will be readily apparent from the following description of the preferred embodiment(s).

DETAILED DESCRIPTION OF THE PREFERRED EMBODIMENT(S)

As previously described, the chemical composition of the present invention is comprised of at least a crosslinking polymer emulsion, a film-forming agent preferably provided as a liquid, and an aqueous carrier. Optionally, the composition further includes a biocide such as a mildewcide, bactericide, and/or fungicide, and optionally also a defoamer.

In the preferred composition, the crosslinking polymer emulsion preferably comprises a crosslinking polyvinyl acetate (PVA) provided as an emulsion, although other known crosslinking or exterior-grade polymers may also be used such as styrene acrylics, vinyl acrylics or acrylics. The polymer should be suitable for exterior uses such as application to new, weathered, and/or rotted wood. The function of the crosslinking polymer emulsion is to promote a tough, durable structure to the composition upon application and drying.

In the preferred embodiment, the polymer emulsion is selected as a "precatalyzed" polymer emulsion, with precatalyzation preferably facilitated by the addition of aluminum chloride to a polymer emulsion. An exemplary precatalyzed crosslinking polymer includes precatalyzed polyvinyl acetate (PVA) emulsion marketed as Vinac® DPM890 DEV brand polymer emulsion by Air Products Corporation of Allentown, Pa. 18195. Vinac® is s registered trademark of Air products for a proprietary PVA polymer emulsion that, according to the manufacturer, is a crosslinkable poly(vinyl acetate) emulsion that is pre-catalyzed and formulated to be ready for use in applications that require a wood adhesive that meets U.S. Type 2 or European D3 water resistance standards. Vinac® DPN890 emulsion is: acidic in nature, can be thickened with hydroxyethyl cellulose, poly(vinyl alcohol) or associative thickeners. Vinac® DPN890 emulsion has been formulated to a minimum film formation temperature of 54° F. (12° C.), and the manufacturer recommends that the application temperature of the adhesive and substrates should be above this temperature. Vinac® DPN890 displays excellent water resistance, and very good heat resistance, good resistance to static load. Vinac® DPN 890 has the following additional properties, according to the manufacturer:

| | |
|---|---|
| Solids | 49 ± 1% |
| Viscosity, cPs 2 | 4,000-6,000 |
| pH | 2.5-3.5 |
| Polymer Type | Vinyl Acetate |
| Protective Colloid | PVOH |
| Mechanical Stability | Excellent |
| Freeze Thaw Stability | Stable |
| Thickening Response | Moderate |
| Reaction to Borax | Coagulates |
| Wet Tack | High |
| Density, lb/gal | 9.0 |

Other suitable commercially available precatalyzed polymer emulsions include, but are not limited to, PD 0312L marketed by HB Fuller Company of St. Paul, Minn. 55110, as well as any crosslinking PVA emulsion sold by National Starch & Chemical Company, Bridgewater N.J. 08807. Preferably, the polymer emulsion comprises between about 40 to about 60 weight percent polymer solids. For example, DPN890 is provided as about 48-50 weight percent polymer solids as supplied by the manufacturer.

As a result of the use of a pre-catalyzed cross-linking polymer emulsion, no significant heat is generated after the product is applied and dries, and no external heat need be applied to cure the applied composition.

The film-forming agent functions to control the open time (i.e. the time before significant crosslinking and curing lead to skin formation of the composition) and therefore promotes excellent penetration of the composition into the wood to be treated. The film-forming agent type and quantity is selected so as to ensure that the composition soaks deeply into the rotted wood and surrounding area before the composition begins to develop a skin. By controlling the rate of skin formation, the film-forming agent allows the composition to penetrate into the rotted wood. This penetration is key to the performance of the composition as a wood rot stabilizer, since only penetrated compositions can reach and will fill deep voids in the rotted area and surrounding wood grains, and then cure to produce a structurally reinforced repair. While some known solventborne stabilizers penetrate deeply into wood as the result of volatile strong organic solvents traveling through and between the wood grain, the inadequate amount of delivered solids, as well as harmful solvent exposure, makes those solventborne products inferior in both terms of performance and safety.

The use of film-forming agents in combination with an aqueous pre-catalyzed polymer emulsion to provide a wood stabilizer is believed by Applicant to be novel. As previously described, the film-forming agent allows for deeper penetration of the composition as opposed to known water-based wood treatment compositions that merely form a dried film on top of the wood's surface. While film-forming agents are commonly used in latex paints, their use in a wood stabilizer and preservative is unprecedented. Film-forming agents (also known as coalescing aids) are necessary additives in latex paints to assist in the film-formation process. For example, the majority of emulsion polymers used in latex paints do not form a film at moderate temperatures, and almost all will not form a film under adverse conditions such as temperatures approaching 0° C. (32° F.) or under high relative humidity. Film-forming agents typically include very slow-evaporating solvents such as glycol ethers, glycol ether esters, and ester alcohols that combine with the emulsified polymer particles and soften them, which reduces the minimum film-formation temperature during the drying process to produce a better film than would otherwise be possible. In addition to lowering the minimum film-formation temperature (MFFT) of latex emulsions, film-forming agents are known to improve weather resistance, scrubbing resistance, and cleanability once cured.

In a preferred embodiment, the film-forming agent is selected from the group consisting of glycol ethers, glycol ether esters, ester alcohols, and combinations thereof. More preferably, the film-forming agent is an ester alcohol liquid such as that film-forming agent marketed under the trade name TEXANOL by the Eastman Chemical Company of Kingsport, Tenn. 37662. TEXANOL is described in Eastman's marketing materials as the chemical 2,2,4-Trimethyl-1,3-pentanediol monoisobutyrate Propionic acid, 2-methyl-, monoester with 2,2,4-trimethyl-1,3-pentanediol Isobutyric acid ester with 2,2,4-trimethyl-1,3-pentanediol.

Water is provided as the solvent carrier for the composition, as well as in the emulsion of the crosslinking polymer. Preferably, the water is deionized. The amount of water provided is adjusted in the composition to provide a desired product consistency and viscosity. Preferably, the composition has a total percent solids range of about 35 to about 50 weight percent, and more preferably in the range of about 40 to about 50 weight percent. Most preferably, the composition contains enough water by weight to provide the composition with a Brookfield LVT viscosity of about 750 to about 1250 cps (using a #2 spindle at 12 rpm at about 25 degrees Celsius.) Other desirable characteristics of the preferred embodiment include a weight per gallon of about 8 to about 10 pounds per gallon, and more preferably about 8.7 to about 9.1 pounds per gallon. The composition further has a pH in the range of about 2.5 to about 3.5, and more preferably in the range about 2.8 to about 3.0.

At least one biocide is optionally provided. The function of the biocide may be selected so as to prevent and/or to inhibit growth of undesirable biological organisms, either in the packaged product and/or in the dispensed and applied composition and/or in the repaired area. The biocide preferably includes at least one of a mildewcide, bactericide, and/or a fungicide due to the nature of the repair—which will customarily, but not necessarily, involve rotted wood resulting from environmental attack such as by water, mold, mildew, fungus, and other known rot producers. The presence of a biocide in the composition provides for immediate chemical attack and remediation of any bacteria, mold, mildew, and/or fungus present in the repair area, and provides long-term protection of the applied composition and the surrounding repaired area as well. A preferred mildewcide is SKANE® M8 brand mildewcide, having an active ingredient of 2-N-OCTYL-4-ISOTHIAZOLIN-3-ONE. SKANE® is a registered trademark of Rohm and Haas of Philadelphia, Pa. Although a functional amount of mildewcide(s) should be used in the present invention, it is preferred that the mildewcide(s) constitute from about 0.05 to about 0.15 weight percent of the wood filler composition.

Optionally, the composition includes a preservative selected to ensure product quality and stability prior to dispensing and application, such as a biocide, bactericide and/or chemical preservatives. Although a functional amount of preservative should be used in the present invention, it is preferred that the preservative constitute(s) from about 0.05 to about 0.20 weight percent of the wood filler composition. It is more preferred that preservative includes at least one biocide. It is most preferred that the biocide is a biocide containing formaldehyde solution 5-chloro-2-methyl-4-isothazolin-3-one, and/or 2-methyl-4-isothiazolin-3-one, such as ACTICIDE® brand pesticide. ACTICIDE® is a registered trademark of THOR AMERICAS, INC. CORPORATION of Trumbull Conn. Alternatively, the biocide may comprise a combination of SPZ-C and Bronopol® brand antimicrobial compound. Bronopol® is a registered trademark of Boots Company Limited of W. Nottingham, UK. The SPZ-C and Bronopol® combination is preferably at about a 1:1 ratio and combined to comprise about 0.05 to about 0.20 weight percent of the composition, with an adjustment to water as necessary to compensate for the increased weight percent of the biocide.

Optionally, the composition further includes ingredients to retard or prevent foaming during manufacture, as well as during shipping and upon application. Preferably, a defoaming agent is provided prior to or during mixing of raw materials incident to manufacture the composition. Most preferably, the defoaming agent is that marketed as Colloids 581b, by Rhodia, Inc. of Cranbury, N.J. 08512.

The following are exemplary of the composition and methods of the invention.

EXAMPLE 1

In a first preferred embodiment of the composition of the present invention, a waterborne rotted wood stabilizer is provided having the following composition by weight percentage: Crosslinking PVA polymer (VINAC® DPN890) about 75 to about 90 percent; Film-forming agent about 0.5 to about 1.5 percent; Bactericide (ACTICIDE® LA) about 0.01 to about 0.1 percent; defoaming agent (Colloids 581b) about 0.01 to about 0.1 percent; mildewcide (SKANE® M-8) about 0.01 to about 0.1 percent; and water about 8 to about 15 percent. The composition preferably has a pH in the range of from about 2.8 to about 3.0. Further the composition preferably has a viscosity of from about 750 to about 1250 cps as measured on a BROOKFIELD RV viscometer (helipath on) with a #2 T/E spindle at 12 rpm and 25° C.

EXAMPLE 2

In a particularly preferred embodiment, the composition of the present invention comprises, on a weight percent basis:

| Item No. | Ingredients | % by Weight |
| --- | --- | --- |
| 1 | Water | 12-15% |
| 2 | ACTICIDE ® LA bactericide | 0.01-0.15% |
| 3 | TEXANOL ® film forming agent | 1.0 to 2.0% |
| 4 | VINAC ® DPN890 PVA emulsion | 82-88% |
| 5 | Colloids 581b defoamer | 0.01-0.10% |
| 6 | SKANE ® M8 mildewcide | 0.01-0.10 |
| | TOTAL: | 100.00 |

The above formulation has a pH of about 2.8-3.0, total solids of about 43.6-47.6%, a viscosity of about 750-1250 cps, white color, and a weight per gallon of about 8.7 to about 9.1 pounds.

The present invention further provides methods for manufacture of the compositions of the present invention. A preferred method for preparing a rotted wood stabilizer composition of the present invention comprises the steps of: (a) providing a mixing vessel; (b) placing water, a defoamer, and at least one crosslinking polymer emulsion in the mixing vessel under slow agitation; (c) mixing this combination of ingredients until substantially homogeneous; (d) adding at least one film-forming agent to the mixing vessel while agitating; (e) mixing the contents of the mixing vessel until substantially homogeneous; and (f) adding water and to the mixing vessel while agitating in sufficient quantity so as to produce a rotted wood stabilizer composition having a viscosity of from about 750 to about 1250 cps and a pH of from about 2.8 to about 3.0.

The method may additionally comprise the step of adding at least one biocide. It is preferred, but not required, that the step of adding at least one biocide is performed at the same time as, or immediately subsequent to, the step of addition of the film-forming agent to the mixing vessel.

The present invention further provides for repair of a rotted or damaged wood component using the compositions of the present invention. First, surfaces to which the rotted wood stabilizer composition of the present invention will be applied should be reasonably clean of dirt, dust, and non-organic contaminants and loose particles. The surface and the stabilizer composition should be at a temperature of 55° F. or warmer. The composition is applied by pouring, brushing, or injecting the composition into the desired repair area. Application of the stabilizer composition should be generous, and any excess can be removed with a rag or other implement known to those in the art of wood repair. The stabilizer composition should be permitted to dry between applications. After finishing a job, application tools and hands can be washed with soap and water before the composition dries.

While the invention has been described in connection with what is presently considered to be the most practical and preferred embodiments, it is to be understood that the invention is not to be limited to the disclosed embodiment(s), but on the contrary, is intended to cover various modifications and equivalent arrangements included within the spirit and scope of the appended claims, which are incorporated herein by reference.

What is claimed is:

1. A rotted wood stabilizer composition, said composition comprising:
    (a) about 75 to about 90 weight percent of a precatalyzed crossliniking polymer emulsion, the emulsion comprising between about 40 and about 60 weight percent polymer solids;
    (b) about 8 to about 15 weight percent water; and
    (c) about 0.5 to about 1.50 weight percent film-forming agent, wherein the composition has a viscosity in the range of about 750 to about 1250 centipoise.

2. The composition of claim 1, wherein the precatalyzed crosslinking polymer is selected from the group consisting of precatalyzed crosslinking polyvinyl acetates, precatalyzed crosslinking styrene acrylics, precatalyzed crosslinking vinyl acrylics, precatalyzed crosslinking acrylics, and combinations thereof.

3. The composition according to claim 1, further comprising at least one biocide.

4. The composition according to claim 3, wherein the biocide is selected from the group consisting of mildewcides, fungicides, bactericides, and combinations thereof.

5. The composition of claim 4, wherein the biocide is present in the range of about 0.01 to about 0.10 weight percent.

6. The composition of claim 1, further comprising a defoaming agent.

7. The composition of claim 6, wherein the defoaming agent is present in the range of about 0.01 to about 0.20 weight percent.

8. The composition of claim 1, wherein said composition has a total solids content in the range of about 40 percent to about 60 percent by weight.

9. The composition of claim 1, wherein said composition has a pH in the range of from about 2.8 to about 3.0.

10. The composition of claim 1, wherein the film-forming agent is selected from the group consisting of glycol ethers, glycol ether esters, ester alcohols, and combinations thereof.

11. A rotted wood stabilizer composition, the composition comprising:
    (a) about 75 to about 90 percent by weight of a precatalyzed crosslinking polymer emulsion, the emulsion comprising in the range of about 40 and about 60 weight percent polymer solids;
    (b) about 0.5 to about 1.5 percent by weight of a film-forming agent;
    (c) about 0.01 to about 0.1 percent by weight of a biocide;
    (d) about 0.01 to about 0.1 percent by weight of a defoaming agent; and
    (e) the balance water,
wherein the composition has a total solids in the range of about 40 to about 60 percent, a pH in the range of from about 2.8 to about 3.0, and a viscosity of from about 750 to about 1250 centipoise.

12. The composition of claim 11, wherein the precatalyzed crosslinking polymer is selected from the group consisting of precatalyzed crosslinking polyvinyl acetates, precatalyzed crosslinking styrene acrylics, precatalyzed crosslinking vinyl acrylics, precatalyzed crosslinking acrylics, and combinations thereof.

13. The composition of claim 11, wherein the film-forming agent is selected from the group consisting of glycol ethers, glycol ether esters, ester alcohols, and combinations thereof.

14. The composition according to claim 11, wherein the biocide is selected from the group consisting of mildewcides, fungicides, and bactericides.

* * * * *

UNITED STATES PATENT AND TRADEMARK OFFICE
CERTIFICATE OF CORRECTION

| | |
|---|---|
| PATENT NO. | : 7,569,157 B2 |
| APPLICATION NO. | : 11/158375 |
| DATED | : August 4, 2009 |
| INVENTOR(S) | : Van R. Foster |

It is certified that error appears in the above-identified patent and that said Letters Patent is hereby corrected as shown below:

Column 7, Line 22, "crossliniking polymer emulsion, the emulsion compris-" should be changed to --crosslinking polymer emulsion, the emulsion compris- --

Signed and Sealed this

Sixth Day of October, 2009

David J. Kappos
*Director of the United States Patent and Trademark Office*